(12) United States Patent
Ikonen et al.

(10) Patent No.: US 9,905,105 B1
(45) Date of Patent: Feb. 27, 2018

(54) METHOD OF INCREASING SENSING DEVICE NOTICEABILITY UPON LOW BATTERY LEVEL

(71) Applicant: General Electric Company, Schenectady, NY (US)

(72) Inventors: Emma Elina Ikonen, Helsinki (FI); Ari Pitkanen, Helsinki (FI); Lauri Aarnio, Helsinki (FI); Erno Muuranto, Helsinki (FI); Elizabeth Devins, Menomonee Falls, WI (US); Robert Filip Arnold Santala, Helsinki (FI)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/366,188

(22) Filed: Dec. 1, 2016

(51) Int. Cl.
  *G08B 21/02* (2006.01)
  *G08B 21/18* (2006.01)
  *G06F 19/00* (2018.01)

(52) U.S. Cl.
  CPC ...... *G08B 21/0211* (2013.01); *G06F 19/3418* (2013.01); *G08B 21/0275* (2013.01); *G08B 21/182* (2013.01)

(58) Field of Classification Search
  CPC .............. G08B 21/0211; G08B 21/182; G08B 21/0275; G06F 19/3418
  See application file for complete search history.

(56) References Cited

U.S. PATENT DOCUMENTS

| | | | |
|---|---|---|---|
| 8,135,415 B2* | 3/2012 | Malik | H04M 1/7253 340/12.5 |
| 8,727,977 B2 | 5/2014 | Banet et al. | |
| 2009/0040041 A1* | 2/2009 | Janetis | G01S 5/0027 340/539.13 |
| 2009/0184825 A1 | 7/2009 | Anderson | |
| 2010/0241290 A1* | 9/2010 | Doane | G05D 1/028 701/2 |
| 2010/0256460 A1 | 10/2010 | Haveri et al. | |
| 2011/0221575 A1* | 9/2011 | Mincey | G06K 19/0716 340/10.3 |
| 2016/0165554 A1 | 6/2016 | Grubis | |
| 2016/0183836 A1 | 6/2016 | Muuranto et al. | |

* cited by examiner

*Primary Examiner* — Brian Wilson
(74) *Attorney, Agent, or Firm* — Andrus Intellectual Property Law, LLP

(57) ABSTRACT

A wireless sensing device and a method for operating a wireless sensing device are described herein. The wireless sensing device includes a battery power supply and a processor that transmits detected physiological parameters from the sensing device to a monitoring device. when the battery level within the sensing device falls below a minimum threshold, the processor of the sensing device reserves a portion of the battery charge to power an indicator to increase the noticeability of the sensing device. The sensing device can also include an RFID tag that is written to by the processor when the state of charge on the battery falls below the minimum threshold. The RFID tag allows RFID detectors to sense the presence of the sensing device without requiring additional battery power.

13 Claims, 5 Drawing Sheets

METHOD OF INCREASING SENSING DEVICE NOTICEABILITY UPON LOW BATTERY LEVEL

BACKGROUND

The present disclosure relates generally to medical devices and, more specifically, to medical monitoring devices for monitoring a patient's physiology and health status.

In the field of medicine, physicians often desire to monitor multiple physiological characteristics of their patients. Oftentimes, patient monitoring involves the use of several separate monitoring devices simultaneously, such as a pulse oximeter, a blood pressure monitor, a heart monitor, a temperature monitor, etc. Several separate patient monitoring devices are often connected to a patient, tethering the patient to multiple bulky bedside devices via physical wiring or cables. Multi-parameter monitors are also available where different sensor sets may be connected to a single monitor. However, such multi-parameter systems may be even more restrictive than separate monitoring devices because they require all of the sensors attached to a patient to be physically attached to a single monitor, resulting in multiple wires running across the patient's body. Thus, currently available patient monitoring devices often inhibit patient movement, requiring a patient to stay in one location or to transport a large monitor with them when they move from one place to another.

Further, currently available monitoring devices are often power intensive and either require being plugged in to a wall outlet or require large battery units that have to be replaced and recharged every few hours. Thus, monitoring multiple patient parameters is power intensive and battery replacement is costly in labor and parts. Thus, frequent monitoring is often avoided in order to limit cost and patient discomfort, and instead patient parameters are infrequently spot checked, such as by periodic nurse visits one or a few times a day. While there are some patients that require continuous, real-time monitoring, such as those patients experiencing a critical health condition, the vast majority of patients need only periodic monitoring to check that their condition has not changed. However, patients that are not being regularly monitored may encounter risky health situations that that go undetected for a period of time, such as where rapid changes occur in physiological parameters that are not checked by a clinician until hours later or until a critical situation occurs.

Presently, wireless patient monitoring systems are being developed in which a wearable sensing device is positioned on the patient to monitor one or more physiological parameters of the patient. The sensing device communicates sensed information to one or more monitoring hubs for analysis and review. Typically, the wireless sensing devices are battery powered and rely upon the battery to provide communication to the monitoring hub.

Since wireless sensing devices are made as small as possible, the wireless monitoring devices can be misplaced, lost or inadvertently removed from the patient environment. This often occurs when a sensor falls off of the patient and becomes concealed within the sheet. The sensor can then be taken out of the room when the sheets are removed from the bed for cleaning. Since the wireless sensing devices are designed for reuse, it is desirable to identify lost sensing devices.

SUMMARY

The present disclosure relates to a patient monitoring system and method. The patient monitoring system includes a monitoring device or monitoring location and one or more sensing devices that are worn by a patient and are operable to transmit measured physiological parameters from the patient to the monitoring device or directly to the network monitoring location.

Each of the sensing devices includes at least one sensor that detects physiological parameters from the patient. The processor of the sensing device receives the detected physiological parameters and operates a wireless transceiver to transmit wireless signals from the sensing device to the monitoring device. A battery contained within the sensing device is used to power both the wireless transceiver and the processor.

The sensing device further includes an indicator that can be operated by the processor when the state of charge of the battery falls below a minimum threshold. The indicator enhances the noticeability of the sensing device and can be used to help in locating a lost sensing device when the state of charge on the battery falls below the minimum threshold. The indicator can be one of multiple different visual indicators, an audible indicator or a tactile indicator, such as a vibration or movement inducing device.

In another embodiment, the sensing device can include an RFID tag. The RFID tag is re-writable such that an emergency message, sensor information or patient information can be stored on the RFID tag. The RFID tag is written by the processor contained within the sensing device at select times during use of the sensing device.

Another embodiment relates to a method of operating the one or more wireless sensing devices to enhance the noticeability of the wireless sensing devices upon a low battery level. When the state of charge of the battery falls below a minimum threshold, the processor contained within the wireless sensing device discontinues normal operation of the wireless transceiver. During this state, the processor activates an indicator to enhance the noticeability of the wireless sensing device. The indicator could be a visual indicator, an audible indicator or any other type of indication that would enhance the noticeability of the wireless sensing device.

In yet another embodiment, the processor of the wireless communication device can write an emergency message or a patient message on an RFID tag contained within wireless sensing device upon the battery charge falling below the minimum threshold. In this manner, the processor can store a static message on the RFID tag such that the static message can be detected by active RFID detectors located within a hospital or facility. The use of the RFID tag allows for enhanced noticeability of the sensing device when the state of charge on the battery falls below a minimum threshold.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

The present inventors have recognized that wireless monitoring systems are desirable for patient comfort, for example to provide more comfort and mobility to the patient being monitored. The patient's movement is not inhibited by wires between sensor devices and/or computing devices that collect and process the physiological data from the patient. Thus, small sensing devices and sensors that can be easily attached to the patient's body are desirable, such as sensing devices that are wearable portable computing devices. In order to do so, the size of the wireless sensing devices must be small. The present inventors have recognized that an important aspect of decreasing the size and weight of wireless sensing devices is decreasing battery size, and that a weakness in the development of wireless sensing devices has been possible misplacement or loss of the sensing devices upon battery depletion.

In view of their recognition of problems and challenges in the development of wireless sensing devices, the present inventors developed the disclosed system and method. As provided herein, the wireless sensing device is designed and operated to enhance the visibility of the wireless sensing device should the wireless sensing device be lost or misplaced. The wireless sensing device withholds a portion of the state of charge on the battery when the wireless sensing device is no longer in communication with a patient monitoring hub. The portion of the retained battery charge is used to generate enhanced indicators and store an emergency message on a re-writable RFID tag that can be read by RFID detectors. In this manner, the wireless sensing devices attempt to draw attention to the device when lost to reduce the likelihood of the wireless sensing devices being permanently misplaced.

Figure 1:
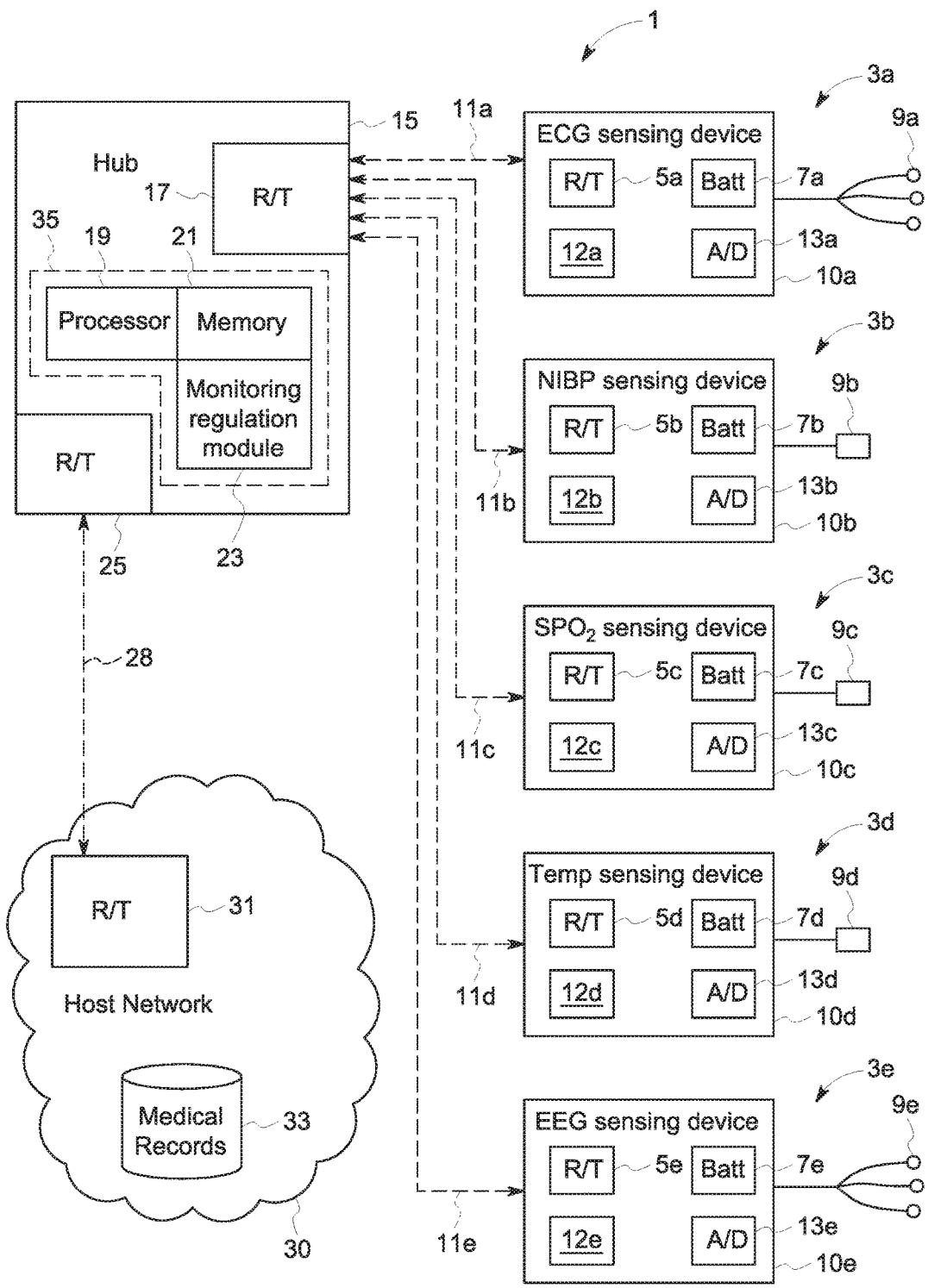
FIG. 1 is an schematic illustration of a patient monitoring system including multiple wireless sensing devices and a collection hub.

FIG. 1 depicts one embodiment of a patient monitoring system 1 containing five wireless sensing devices 3a-3e in wireless communication with a hub 15. The hub 15 is in wireless communication with a host network 30 that contains medical records database 33. For example, the hub device 15 may be attached to the patient's body, placed on or near the patient's bed, or positioned within range of the patient, such as in the same room as the patient. The hub device 15 may be a separate, stand alone device, or it may be incorporated and/or housed with another device within the system 1, such as housed with one of the wireless sensing devices 3a-3e. Each wireless sensing device 3a-3e contains one or more sensors 9a-9e for measuring a physiological parameter from a patient, and also includes a base unit 10a-10e that receives the physiological parameter measurements from the sensors 9a-9e and transmits a parameter dataset based on those measurements to the hub device 15 via communication link 11a-11e. The sensors 9a-9e may be connected to the respective base unit 10a-10e by wired or wireless means. The sensors 9a-9e may be any sensors, leads, or other devices available in the art for sensing or detecting physiological information from a patient, which may include but are not limited to electrodes, lead wires, or available physiological measurement devices such as pressure sensors, flow sensors, temperature sensors, blood pressure cuffs, pulse oximetry sensors, or the like.

In the depicted embodiment, a first wireless sensing device 3a is an ECG sensing device 9a having sensors 9a that are ECG electrodes. A second wireless sensing device 3b is a non-invasive blood pressure (NIBP) sensing device with a sensor 9b that is a blood pressure cuff including pressure sensors. A third wireless sensing device 3c is a peripheral oxygen saturation (SpO2) monitor having sensor 9c that is a pulse oximetry sensor, such as a standard pulse oximetry sensor configured for placement on a patient's fingertip. A fourth wireless sensing device 3d is a temperature monitor having sensor 9d that is a temperature sensor. The depicted embodiment of the system 1 further includes a fifth wireless sensing device 3e that is an EEG monitor having sensors 9e that are EEG electrodes. It should be understood that the patient monitoring system 1 of the present disclosure is not limited to the examples of sensor devices provided, but may be configured and employed to sense and monitor any clinical parameter. The examples provided herein are for the purposes of demonstrating the invention and should not be considered limiting.

The base units 10a-10e of each of the exemplary wireless sensing devices 3a-3e may include analog-to-digital (A/D) converters 13a-13e, which may be any devices or logic sets capable of digitizing analog physiological signals recorded by the associated sensors 9a-9e. For example, the A/D converters 13a-13e may be Analog Front End (AFE) devices. The base units 10a-10e may further include processors 12a-12e that receive the digital physiological data from the A/D converters 13a-13e and create a parameter dataset for transmission to the hub device 15 and for the host network 30. Each base unit 10a-10e may be configured differently depending on the type of wireless sensing device, and may be configured to perform various signal processing functions and or sensor control functions. To provide just a few examples, the processor 12a in the ECG sensing device 3a may be configured to filter the digital signal from the ECG sensors 9a to remove artifact and/or to perform various calculations and determinations based on the recorded cardiac data, such as heart rate, QRS interval, ST-T interval, or the like. The processor 12b in the NIBP monitor 3b may be configured, for example, to process the physiological data recorded by the sensors 9b in a blood pressure cuff to calculate systolic, diastolic, and mean blood pressure values for the patient. The processor 12c of the SpO2 sensing device 3c may be configured to determine a blood oxygenation value for the patient based on the digitized signal received from the pulse oximetry sensor 9c. The processor 12d of the temperature sensing device 3d may be configured to, for example, determine a temperature for the patient, such as a mean temperature based on the digitized temperature data received from the thermal sensor 9d. And the process or 12e of the EEG sensing device 3e may be configured, for example, to determine a depth of anesthesia measurement value, such as an entropy value or a sedation responsiveness index value.

Accordingly, the processor 12a-12e may develop a datasets that, in addition to the recorded physiological data, also include values measured and/or calculated from the recorded physiological data. The respective processors 12a-12e may then control a receiver/transmitter 5a-5e in the relevant wireless sensing device 3a-3e to transmit parameter datasets to the hub device 15 via communication link 11a-11e. The parameter dataset transmitted from the respective wireless sensing devices 3a-3e may include the raw digitized physiological data, filtered digitized physiological data, and/or processed data indicating information about the respective physiological parameter measured from the patient.

In other embodiments, the processors 12a-12e may not perform any signal processing tasks and may simply be configured to perform necessary control functions for the respective wireless sensing device 3a-3e. In such an embodiment, the parameter data set transmitted by the respective processor 12a-12e may simply be the digitized raw data or digitized filter data from the various sensor devices 9a-9e.

Each wireless sensing device 3a-3e includes a battery 7a-7e that stores energy and powers the various aspects of the wireless monitor. Each processor 12a-12e may further include power management capabilities, especially where the respective wireless sensing device 3a-3e contains more demanding electromechanical aspects. Each processor 12a-12e may monitor a battery status 43 (FIG. 3), such as a charge level of the relevant battery 7a-7e. The processor 12a-12e may communicate the battery status to the hub device 15 by the communication link 11a-11e. Alternatively or additionally, the processor 12a-12e may control a local display on the wireless sensing device 3a-3e to display the battery status 43, and/or may control the emission of an audio and/or visual alert regarding the battery status 43.

The receiver/transmitter 5a-5e of each wireless sensing device 3a-3e communicates via the respective communication link 11a-11e with the receiver/transmitter 17 of the hub device 15, which may include separate receiving and transmitting devices or may include an integrated device providing both functions, such as a transceiver. The receiver/transmitters 5a-5e of the wireless sensing devices 3a-3e and the receiver/transmitter 17 of the hub device 15 may be any radio frequency devices known in the art for wirelessly transmitting data between two points. In one embodiment, the receiver/transmitters 5a-5e and 17 may be body area network (BAN) devices, such as medical body area network (MBAN) devices, that operate as a wireless network. For example, the wireless sensing devices 3a-3e may be wearable or portable computing devices in communication with a hub device 15 positioned in proximity of the patient. Other examples of radio protocols that could be used for this purpose include, but are not limited to, Bluetooth, Bluetooth Low Energy (BLE), ANT, and ZIGBEE.

The hub device may further include computing system 35 having processor 19 and memory 21. The hub device 15 may serve to control the wireless sensing devices 3a-3e, and thus may transmit operation commands 45a-45e (FIG. 3) to the respective wireless sensing devices 3a-3e via the communication link 11a-11e to control their monitoring operations. The hub 15 may contain a monitoring regulation module 23 that is a set of software instructions stored in memory and executable on the processor 19 to assess the physiological data collected by the wireless sensing devices 3a-3e and determine a patient condition therefrom, and to control the respective wireless sensing devices 3a-3e according to the patient condition.

The hub device 15 may communicate with a host network 30 via a wireless communication link 28, such as to transmit the parameter datasets for the respective wireless sensing devices 3a-3e for storage in the patient's medical record. The hub 15 has receiver/transmitter 25 that communicates with a receiver/transmitter 31 associated with the host network 30 on communication link 28, which may operate according to a network protocol appropriate for longer-range wireless transmissions, such as on the wireless medical telemetry service (WMTS) spectrum or on a Wi-Fi-compliant wireless local area network (LAN). The host network 30 may be, for example, a local computer network having servers housed within a medical facility treating the patient, or it ma be a cloud-based system hosted by a cloud computing provider. The host network 30 may include a medical records database 33 housing the medical records for the patient, which may be updated to store the parameter datasets recorded and transmitted by the various wireless sensing devices 3a-3e. The host network 30 may further include other patient care databases, such as for monitoring, assessing, and storing particular patient monitoring data. For example, the host network may include an ECG database, such as the MUSE ECG management system produced by General Electric Company of Schenectady, N.Y.

In various embodiments, the hub device 15 may contain software for processing the physiological signals recorded by the various wireless sensing devices 3a-3e. For example, in one embodiment the individual wireless sensing device 3a-3e may perform minimal or no signal processing on the physiological data measured from the patient, and may simply transmit the digitized physiological data recorded from the respective sensors 9a-9e. Software stored in the hub device 15 may then be executed on the processor 19 to calculate various useful parameters from the physiological data, as is explained above with respect to the exemplary wireless sensing devices 3a-3d depicted in FIG. 1. In still other embodiments, minimal or no signal processing may be performed in the hub device 15, and the hub 15 may simply serve to relay the parameter datasets from the wireless sensing devices 3a-3e to the host network 30. In such an embodiment, the computing system 35, including the monitoring regulation module 23, may reside in the host network 30.

Figure 2:
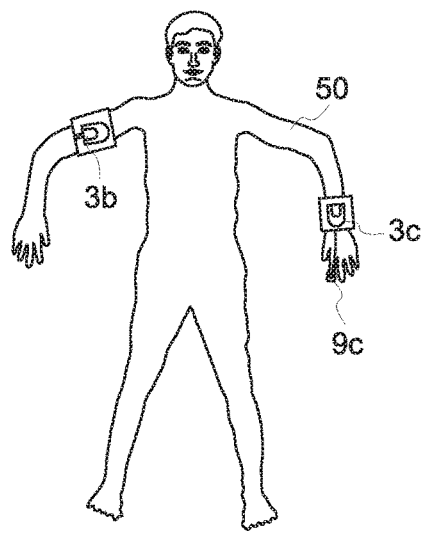
FIG. 2 is a view of a patient wearing two wireless sensing devices.

In FIG. 2, a patient 50 may be monitored by two or more sensor devices 3, such as a non-invasive blood pressure sensor device 3b and a pulse oximeter sensor device 3c. Each of the sensor devices 3b, 3c operate to collect physiological signals from the patient 50 and transmit the signals to the hub 15 as described in FIG. 1. In an embodiment where the hub 15 is part of a body area network (BAN), the hub 15 would be in a location near the patient, such as attached to the patient's body, placed on or near the patient's bed, or positioned within range of the patient such as in the same room as the patient.

Figure 3:
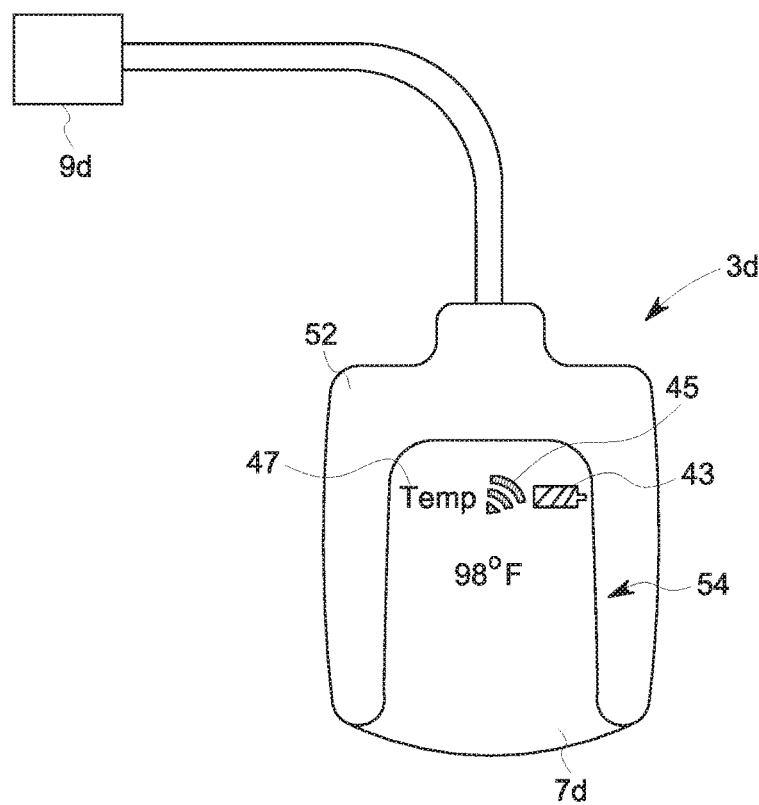
FIG. 3 is a view of one of the wireless sensing devices including a battery having an external display.

FIG. 3 illustrates one embodiment of a wireless sensing device 3d that is used to monitor the temperature of the patient. The temperature sensing device 3d includes the sensor 9d that is positioned on the patient and communicates electrical signals that correlate to the temperature of the patient being sensed. The wireless sensing device 3d includes a removable battery pack 7d that is received within a main body portion 52. In the embodiment illustrated, the battery pack 7d includes a display 54 that includes the battery indicator 43, the wireless signal strength indicator 45 and a physiological temperature output display 47. It should be appreciated, however, that the wireless sensing device 3 may include a display 54 separate from the battery pack 7d. The combination of the wireless sensing device 3 and battery pack 7d can be configured to generate a "low battery" alert either on the display 54 or through a communication to the hub, or both. As can be understood in FIG. 3, the size of the wireless sensing device 3d is small enough that it could be lost in sheets or articles of clothing.

Figure 4:
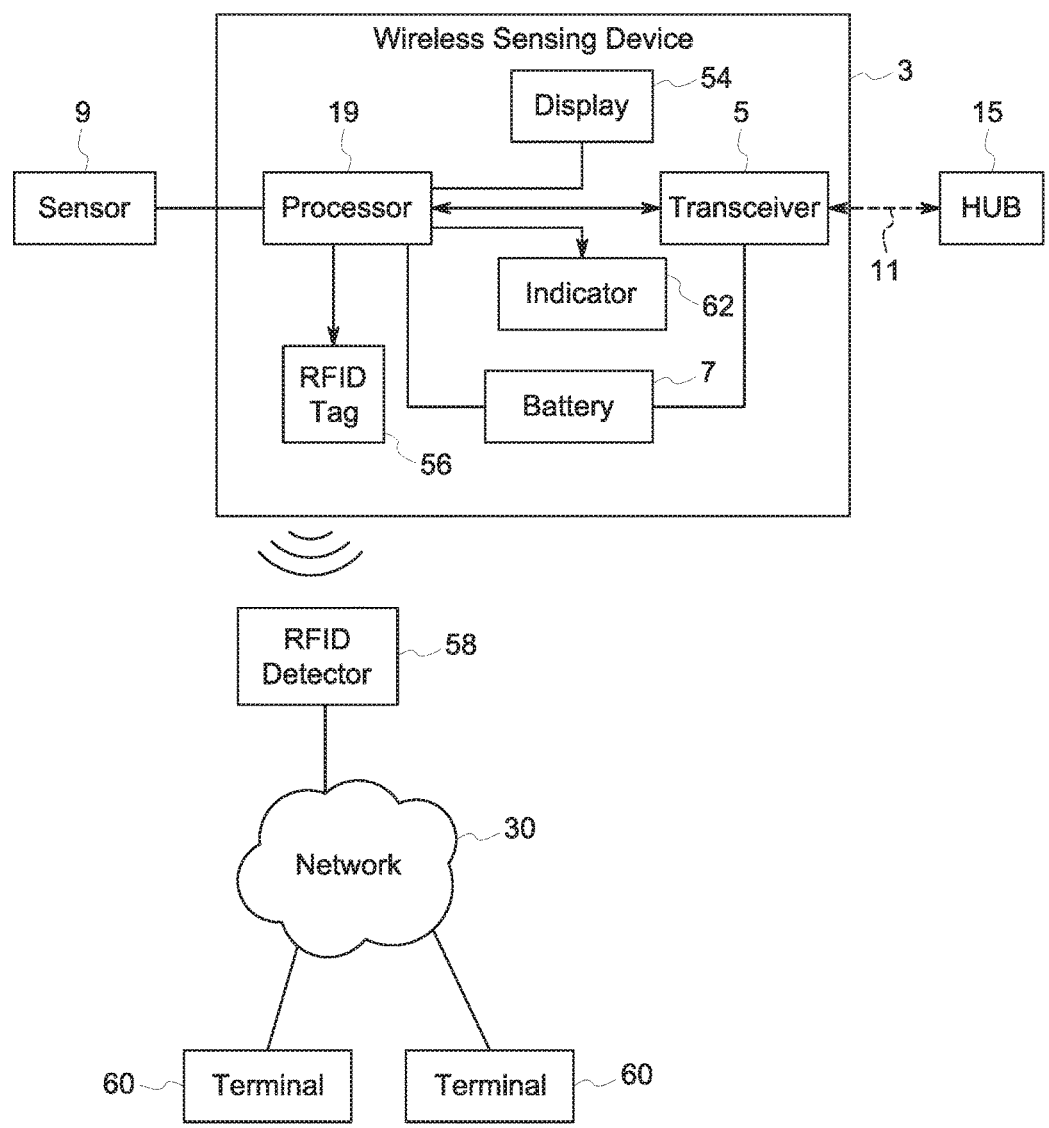
FIG. 4. is a schematic illustration of the operating components of one of the wireless sensing devices and the communication from the sensing device.

FIG. 4 provides a schematic illustration of one embodiment of a wireless sensing device 3 constructed in accordance with the present disclosure. The wireless sensing device 3 shown in FIG. 4 is meant to depict any one of the multiple types of wireless sensing devices shown and described in FIG. 1. In the embodiment shown in FIG. 4, the wireless sensing device 3 communicates through a wireless communication link 11 to the hub 15. However, it is contemplated that the wireless sensing device 3 could communicate directly to the hospital network 30 or any other hub located within the communication range of the wireless sensing device 3.

As described previously, the wireless sensing device 3 includes a transceiver 5 that is able to both receive and transmit wireless communication signals. The wireless transceiver 5 is connected to the processor 19 such that the processor 19 can receive the wireless signals received from the hub 15. In addition, the processor 19 is able to transmit wireless communication signals through the transceiver 5 for receipt at the hub 15 or the hospital information system. The processor 19 is powered by the battery 7 which can be included internally within the wireless sensing device 3 or could be removably received within a battery slot formed in the main body of the sensing device. The battery 7 provides the required power for operating the processor 19 as well as the transceiver 5. The processor 19 monitors the state of charge on the battery 7 which can be shown on the display 54 (FIG. 3). As described and shown in FIG. 3, the display 54 can be included as part of the wireless sensing device 3 or could be included on the battery 7 and can include a battery indicator 43.

During operation of the wireless sensing device, the wireless sensing device 3 communicates using wireless communications to the hub 15 to both relay information to the hub 15 as well as receive communication feedback from the hub 15. During this wireless communication, the hub 15 is able to identify the specific wireless sensing device 3 and provide information about the wireless sensing device to the hospital information system. In this manner, the hospital information system can monitor the status of the sensing device 3 and determine the physical location of each of the wireless sensing devices 3 throughout the hospital environment.

During operation of the wireless sensing device, the battery 7 is continually discharging to provide the operative power for the processor 19 and the transceiver 5. When the state of charge on the battery 7 begins to drop, the processor 19 can generate a message that is received by the hub 15 indicating that the wireless sensing device 3 needs recharging. The hub 15 or the hospital information system can then send alerts or alarms indicating the need for recharging. However, if the wireless sensing device 3 is out of communication range with the hub 15 or any other hub, the transceiver 5 will continue to try to establish a communication link. Such unsuccessful communication attempts will continue to discharge the battery until the battery reaches a charge state in which any further operation of the transceiver 5 will completely discharge the battery and render the entire wireless sensing device 3 inoperable.

In a situation in which the wireless sensing device 3 ends up in a trash bin, laundry basket or any other undesirable location, it is desirable to prevent the battery 7 from completely discharging and thus being completely unable to communicate to either the hub 15 or any other communication device.

In the embodiment shown in FIG. 4, the wireless sensing device 3 includes an RFID tag 56 that is in communication with the processor 19. It is contemplated that the RFID tag could be a re-writable RFID tag that can include a message delivered from the processor 19. As an illustrative example, the RFID tag 56 could be a re-writable RFID tag that can be written as many as 5,000-10,000 times during its life cycle. After the RFID tag 56 is written by the processor 19, the RFID tag 56 forms a passive device that can be read by an active RFID detector 58, such as illustrated in FIG. 4. As is well known, the active RFID detector 58 generates excitation energy that is received by the RFID tag 56 when the RFID tag 56 is in close proximity to the RFID detector 58. The passive RFID tag 56 will allow detection of the wireless sensing device 3 even when the battery 7 has been completely discharged.

When the RFID detector 58 senses the RFID tag 56, the RFID detector 58 can read the information stored on the tag and communicate this information through the host network 30 to one or more monitoring terminals 60. It is contemplated that the processor 19 could write various different types of information on the RFID tag 56 that would allow the host network 30, and the individuals at the various terminals 60, to identify the location of a lost wireless sensing device 3 by its detection by the RFID detector 58. It is contemplated that RFID detectors 58 could be located at various locations within a hospital, such as at the entry to each patient ward, near various nursing stations, near a laundry facility or at any other location where it would be beneficial to position an RFID detector 58 to sense various different types of RFID devices that include RFID tags 56, such as the wireless sensing device 3.

In addition to including messages about the state of charge of the battery 7, the RFID tag 56 could include other information specific to the patient or the device. Since the wireless sensing device 3 is to be worn by the patient, patient related information could be stored on the RFID tag 56 and read by the various RFID detectors 58. As an example, the RFID tag 56 could include information that would restrict the operation of doors, elevators or other access points to prevent the patient from wandering into areas of the hospital outside of a prescribed location. In addition, the RFID tag 56 could include medical information about the patient such that this emergency information could be detected and determined immediately by the RFID detector. Since the RFID tag 56 is re-writable, the processor 19 can store any desired information on the RFID tag 56 which can then be passively read by the RFID detector 58.

Although an RFID tag 56 is shown in the embodiment of FIG. 4, it should be understood that the RFID tag 56 could be eliminated or not included in the sensing device 3 while still operating within the scope of the present disclosure.

In the embodiment shown in FIG. 4, the wireless sensing device 3 further includes an indicator 62 that is operable by the processor 19 to generate some type of indication of an emergency or lost condition of the wireless sensing device 3. It is contemplated that the indicator 62 could generate a flashing light, change the color of an operating light, generate an audible message or warning or be a display screen that changes colors depending upon the state of the wireless sensing device 3. In the embodiment shown in FIG. 4, a display 54 is also associated with the wireless sensing device 3. The display 54 could work either with the indicator 62 or in place of the indicator 62 to generate some type of signal or message that would draw attention to the wireless sensing device 3 which would allow the wireless sensing device 3 to be more easily located when lost. In accordance with the present disclosure, it is contemplated that a flashing rescue message could be shown on the display 54 at set intervals or that a rescue message could be permanently displayed on an e-ink display 54. In each of these alternate configurations, the indicator 62 would generate some type of emergency indicator when the wireless sensing device 3 was "lost" and when the state of charge of the battery 7 is at a critically low level. It is contemplated that a "lost" state occurs whenever the sensing device 3 is out of communication range with any of the hubs 15 or the hospital network.

Figure 5:
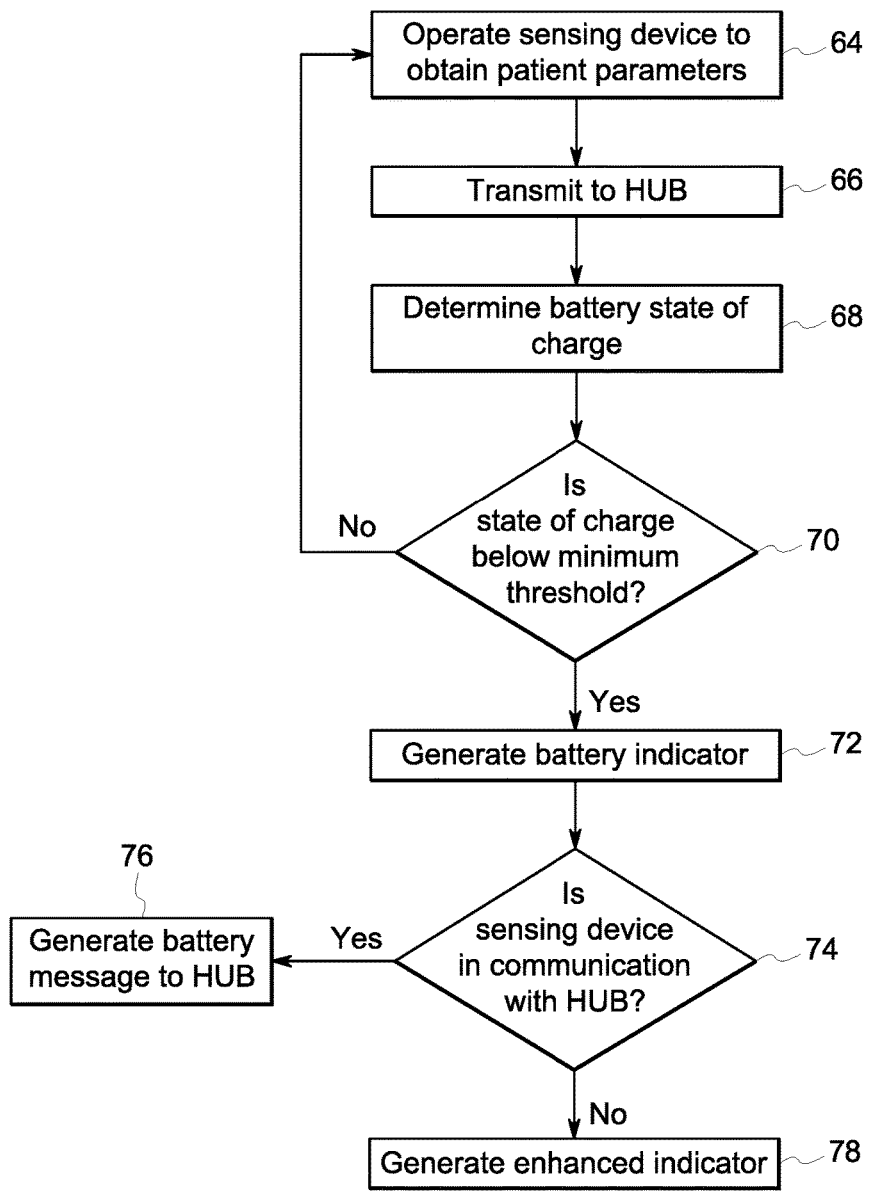
FIG. 5 is a flowchart illustrating the method of operation in one embodiment of the present disclosure.

FIG. 5 illustrates a process flow diagram of one mode of operating the wireless sensing device 3 shown in the drawing Figures. In the mode of operation shown in FIG. 5, the processor 19 initially operates to obtain patient parameters through the sensor 9, as illustrated in step 64. Once the processor receives the information from the sensor, the processor transmits the information to the hub through the wireless transceiver, as illustrated in step 66. Typically, the wireless transmission from the transceiver 5 to the hub 15 occurs over a relatively short distance, such as within the room of a patient. The transmission of the information from the processor to the hub 15 occurs continuously or at a defined period depending upon the operation of the wireless sensing device. During this transmission, the hub 15 is able to confirm the identity and location of the sensing device 3 and report this information as needed.

In step 68, the processor 19 in the sensing device 3 determines the state of charge on the battery. Initially, the battery will be charged to 100% of its charged capacity and will discharge as the battery is used to drive all of the operating components of the wireless sensing device 3. As described in FIG. 3, the processor 19 can be used to control the output of the display 54, which can include the battery indicator 43. In addition, the processor can communicate the state of charge of the battery to the hub 15 utilizing the transceiver 5.

After determining the state of battery charge in step 68, the processor determines in step 70 whether the state of charge is below a minimum threshold. Since the wireless sensing device 3 is a small component and is battery-powered, it is contemplated that the processor will discontinue normal operation of the wireless transceiver and other components of the wireless sensing device when the state of charge of the battery reaches a minimum, emergency threshold. As an illustrative example, the minimum battery threshold set in step 70 could be 5% of the total charge of the battery. However, smaller amounts, such as 1-2% could be used as the minimum threshold in step 70. The minimum threshold must be above the required battery charge that is needed for the battery 7 to power the processor 19 to generate an emergency indicator message for a determined period of time. This period of time could be several days, which would provide an acceptable amount of time to locate the sensing device 3 should the sensing device 3 be misplaced. The processor 19 will discontinue normal operation of the transceiver 5 once the battery state of charge reaches the minimum threshold. This normal operation typically includes data transmissions that could be received by one of the hubs 15.

If the processor determines in step 70 that the state of charge of the battery is not below the minimum threshold, the processor will return to step 64 and monitor the physiological parameters of the patient as normal. If the sensing device 3 is disconnected from the patient and the state of charge is above the minimum threshold, the processor and transceiver will continue to attempt to create a communication link with one of the hubs 15.

If the processor determines in step 70 that the state of charge is below the minimum threshold, the processor will enter an emergency state and generate a first indicator signal as shown in step 72. The first indicator generated in step 72 could simply be a flashing battery indicator light 43 shown in FIG. 3.

In step 74, the processor determines whether the sensing device is able to communicate with one or more of the monitoring hubs 15. If such communication is possible, the processor will generate an emergency battery message to the hub, as shown in step 76. However, if the sensing device 3 is not in range of any of the monitoring hubs 15, such status indicates that the wireless sensing device 3 may be lost or in an undesired location. In such a case, the processor will continue to step 78 and generate an enhanced indicator. As described previously, the enhanced indicator may result in a flashing message, a flashing display, a change of appearance of the sensing device or any other type of high visibility indicator that may draw attention to the sensing device. The processor will generate the enhanced indicator in step 78 only when the battery charge is below the minimum threshold and the sensing device is not in communication with any one of the hubs 15. In this manner, the last portion of the state of charge of the battery can be used to attempt to draw attention to the sensing device to increase the chances that the sensing device can be located after being lost.

Figure 6:
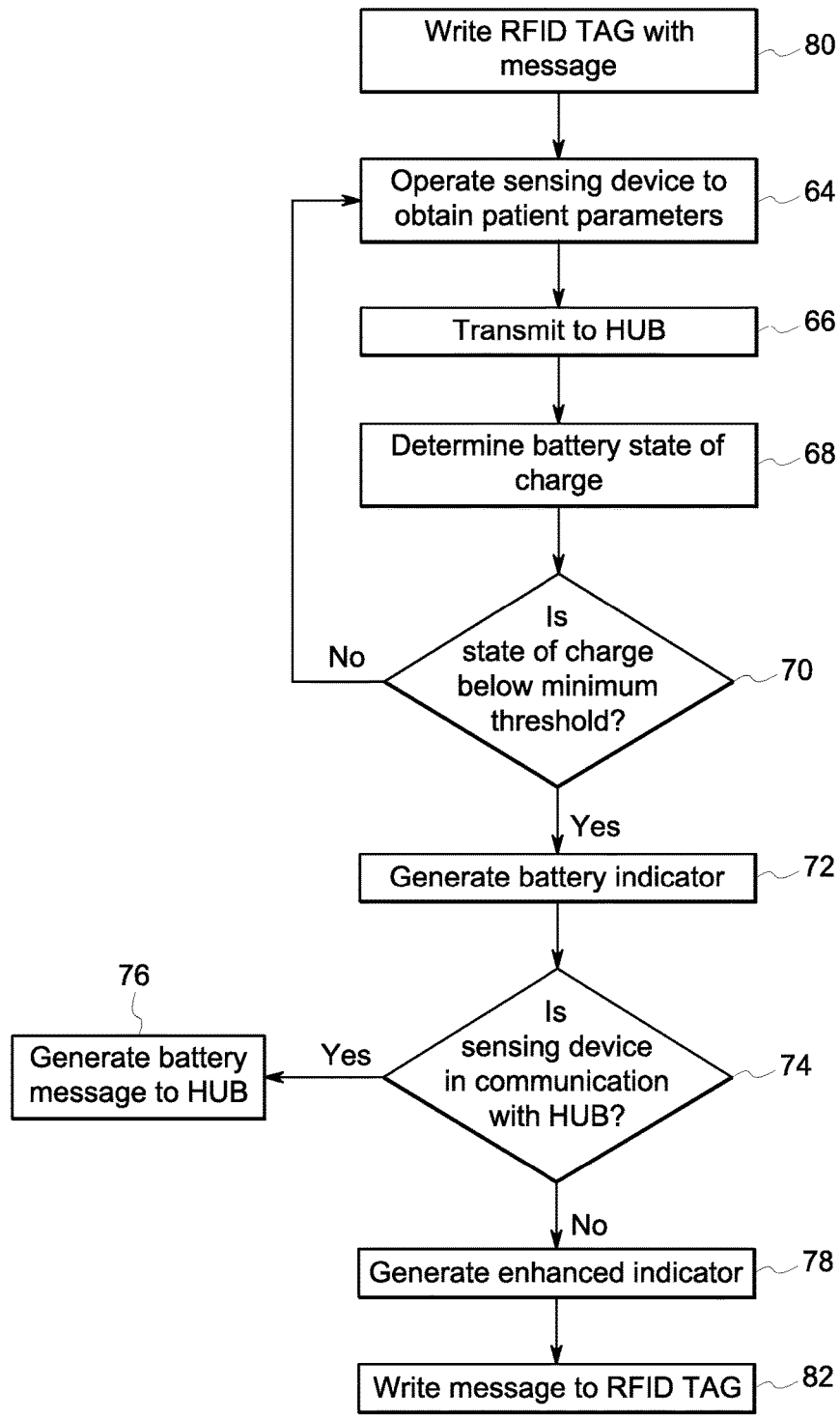
FIG. 6 is a flowchart illustrating the method of operation in a second embodiment of the present disclosure.

FIG. 6 illustrates a second contemplated flow diagram illustrating a second mode of operation when the wireless sensing device 3 shown in FIG. 4 includes a re-writeable RFID tag 56.

In the flow diagram shown in FIG. 6, the processor 19 initially writes information to the RFID tag 56 when the sensing device is activated, as shown by step 80. The information written by the processor 19 could include various different types of information related to either the patient or the sensing device. As an illustrative example, the processor 19 could record patient identification information onto the RFID tag along with identification information about the sensor and the location of the hub that is associated with the specific sensing device including the RFID tag. Further, the RFID tag could include information as to allowed and restricted areas for the patient. For example, if the sensing device were utilized with a patient having dementia, the RFID tag could be written with instructions that would prevent opening and closing of doors from a patient ward. In patient wards that include patients that could wander, an RFID detector would be positioned near the doors of the patient ward and the sensing device could then be used to allow and restrict access to patients from entering and leaving the specific ward. As described previously, when the patient having the wireless sensing device 3 passes by an RFID detector, the RFID detector 58 will sense the written information on the tag and contact the host network for response accordingly.

Once the RFID tag has been written in step 80, the system carries out steps 64-78 as described in the flow diagram of FIG. 5.

In the embodiment shown in FIG. 6, in addition to generating the enhance indicator in step 78, the processor proceeds to step 82 and writes an emergency message to the RFID tag. The emergency message written to the RFID tag in step 82 is a result of the charge on the battery falling below a minimum threshold and the sensing device being out of communication with the hub. The message written in step 82 is an emergency message that can be read by any of the RFID detectors 58 located within the hospital. When the RFID detector located in the hospital reads the message written in step 82, the RFID detector can communicate information to the hospital network and provide information as to the location of the previously lost sensing device. Since the state of charge on the battery has fallen below the minimum threshold, the processor will no longer attempt to generate wireless signals through the transceiver 5 to the hub 15. Instead, the remaining battery life will be utilized to generate the enhanced indicator in step 78 as well as to write the RFID message in step 82.

As can be understood by the above description, the wireless sensing device utilizes the processor to restrain the last portion of battery power to attempt to generate an enhanced indicator such that the wireless sensing device can be located when lost. In addition, the emergency message written to the RFID tag may help in identifying the lost sensing device when the sensing device passes by one of numerous RFID detectors located within the hospital environment.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A sensing device configured to be worn by a patient and operable to measure at least one physiological parameter from the patient and transmit the measured physiological parameter to a monitoring device, comprising:
    at least one sensor for detecting the physiological parameter from the patient;
    a processor for receiving the detected physiological parameter;
    a wireless transceiver for transmitting wireless signals from the processor to the monitoring device;
    a battery;
    an indicator operable by the processor when a state of charge of the battery falls below a minimum threshold; and
    a re-writeable passive RFID tag,
    wherein the processor is operable to write an emergency message on the RFID tag when the state of charge of the battery falls below the minimum threshold, wherein the emergency message is unrelated to the state of charge of the battery.

2. The sensing device of claim 1 wherein the minimum threshold is the state of charge required to operate the wireless transceiver to transmit the wireless signals.

3. The sensing device of claim 1 wherein the indicator is a visual indicator.

4. The sensing device of claim 1 wherein the processor is operable to write a patient message on the RFID tag that includes information describing the patient.

5. A method of monitoring a patient, the method comprising the steps of:
    operating each of one or more wireless sensing devices to measure a physiological parameter from the patient and wirelessly transmit patient monitoring signals to a monitoring device;
    determining a state of charge of a battery associated with the wireless sensing device;
    generating an indicator signal from the wireless sensing device when the state of charge falls below a minimum threshold required to communicate with the monitoring device;
    writing an emergency message to an RFID tag of the wireless sensing device when the state of charge falls below the minimum threshold, wherein the emergency message is unrelated to the state of charge of the battery and includes information describing the patient.

6. The method of claim 5 further comprising the step of discontinuing communication with the monitoring device when the state of charge of the battery falls below the minimum threshold to limit the further discharge of the battery.

7. The method of claim 5 further comprising the steps of:
    attempting to communicate with the monitoring device when the state of charge of the battery falls below the minimum threshold; and
    discontinuing communication attempt with the monitoring device upon a failed communication attempt to conserve the state of charge of on the battery.

8. The method of claim 5 wherein the indicator signal is a visual indicator.

9. The method of claim 5 further comprising the step of writing a patient message on the RFID tag, wherein the patient message includes location restrictions for the patient.

10. The method of claim 5 wherein the indicator signal is generated when the wireless sensing device is out of communication with the monitoring device.

11. A method of monitoring a patient, the method comprising the steps of:
    operating each of one or more wireless sensing devices to measure a physiological parameter from the patient and wirelessly transmit patient monitoring signals to a monitoring device;
    determining a state of charge of a battery associated with the wireless sensing device;
    generating an indicator signal from the wireless sensing device when the state of charge falls below a minimum threshold;
    attempting to communicate between the wireless sensing device and the monitoring device;
    writing an emergency message to an RFID tag of the wireless sensing device when the state of charge falls below the minimum threshold and upon failure to communicate with the monitoring device, wherein the emergency message is unrelated to the state of change of the battery and includes information describing the patient; and
    generating an enhanced indicator signal that is different from the indicator signal when the state of charge falls below the minimum threshold and upon failure to communicate with the monitoring device.

12. The method of claim 11 further comprising the step of writing an information message to the RFID tag upon initial operation of the wireless sensing device.

13. The method of claim 12 wherein the information message comprises patient information including patient restrictions.

* * * * *